United States Patent
Winkler

(12) 
(10) Patent No.: US 6,411,851 B1
(45) Date of Patent: Jun. 25, 2002

(54) IMPLANTABLE MEDICAL DEVICE PROGRAMMING APPARATUS HAVING AN AUXILIARY COMPONENT STORAGE COMPARTMENT

(75) Inventor: Thomas J. Winkler, Isanti, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/433,477

(22) Filed: Nov. 4, 1999

(51) Int. Cl.$^7$ .................................................. A61N 1/37
(52) U.S. Cl. ......................................................... 607/30
(58) Field of Search ............................. 607/30, 32, 36, 607/59, 142, 2, 5; 206/828, 438, 363, 570

(56) References Cited

U.S. PATENT DOCUMENTS

| | | | |
|---|---|---|---|
| 4,208,008 A | 6/1980 | Smith ........................... 371/15 |
| 4,233,985 A | 11/1980 | Hartlaub et al. ............. 128/419 |
| 4,236,524 A | 12/1980 | Powell et al. ................ 128/419 |
| 4,250,884 A | 2/1981 | Hartlaub et al. ............. 128/419 |
| 4,253,466 A | 3/1981 | Hartlaub et al. ............. 128/419 |
| 4,273,132 A | 6/1981 | Hartlaub et al. ............. 128/419 |
| 4,273,133 A | 6/1981 | Hartlaub et al. ............. 128/419 |
| 4,316,472 A | 2/1982 | Mirowski et al. ............ 128/419 |
| 4,374,382 A | 2/1983 | Markowitz ............. 340/870.01 |
| 4,375,817 A | 3/1983 | Engle et al. .................. 128/419 |
| 4,379,459 A | 4/1983 | Stein ............................ 128/419 |
| 4,384,585 A | 5/1983 | Zipes ........................... 128/419 |
| 4,476,868 A | 10/1984 | Thompson .................... 128/419 |
| 4,556,063 A | 12/1985 | Thompson et al. .......... 128/419 |
| 4,577,633 A | 3/1986 | Berkovits et al. ............ 128/419 |
| 4,587,970 A | 5/1986 | Holley et al. ................. 128/419 |
| RE32,361 E | 2/1987 | Duggan ........................ 128/696 |
| 4,726,380 A | 2/1988 | Vollmann et al. ............ 128/419 |
| 4,727,877 A | 3/1988 | Kallok ......................... 128/419 |
| 4,821,723 A | 4/1989 | Baker, Jr. et al. ............ 128/419 |
| 4,830,006 A | 5/1989 | Haluska et al. .............. 128/419 |
| 4,880,005 A | 11/1989 | Pless et al. ................... 128/419 |
| 4,949,719 A | 8/1990 | Pless et al. ................... 128/419 |
| 4,953,551 A | 9/1990 | Mehra et al. ................. 128/419 |
| 5,099,838 A | 3/1992 | Bardy .......................... 128/419 |
| 5,117,824 A | 6/1992 | Keimel et al. ............... 128/419 |
| 5,131,388 A | 7/1992 | Pless et al. ................... 128/419 |
| 5,144,949 A | 9/1992 | Olson .......................... 128/419 |
| 5,158,078 A | 10/1992 | Bennett et al. .............. 128/419 |
| 5,163,427 A | 11/1992 | Keimel ........................ 128/419 |
| 5,188,105 A | 2/1993 | Keimel ........................ 128/419 |
| 5,199,428 A | 4/1993 | Obel et al. ................... 128/419 |
| 5,207,218 A | 5/1993 | Carpentier et al. .......... 128/419 |
| 5,269,298 A | 12/1993 | Adams et al. ............... 128/419 |
| 5,312,453 A | 5/1994 | Shelton et al. ................ 607/19 |

(List continued on next page.)

OTHER PUBLICATIONS

"Onset and Stability for Ventricular Tachyarrhythmia Detection in an Implantable Pacer –Cardioverter–Defibrillator," by Olson et al., published in Computers In Cardiology, Oct. 7–10, 1986, IEEE Computer Society Press, pp. 167–170.

"Automatic Tachycardia Recognition," by Arzbaecher et al., published in PACE, May–Jun., 1984, pp. 541–547.

*Primary Examiner*—George R. Evanisko
*Assistant Examiner*—Kristen Droesch
(74) *Attorney, Agent, or Firm*—Girma Wolde-Michael

(57) ABSTRACT

A portable programming apparatus for use with an implantable medical device is disclosed. The programming apparatus includes a housing, at least one auxiliary component, and a lip. The housing contains computer circuitry and defines a storage compartment. The auxiliary/y component is configured to assist with programming an implantable medical device, perform programming and data transmission functions in cooperation with a remote data center, and interfaces with the computer circuitry via an associated cable. The lip is configured to extend along at least a portion of a perimeter of the storage compartment. With this configuration, the lip selectively maintains the cable within the storage compartment thereby minimizing potential damage to the cable.

68 Claims, 10 Drawing Sheets

U.S. PATENT DOCUMENTS

| | | | |
|---|---|---|---|
| 5,314,430 A | 5/1994 | Bardy | 607/5 |
| 5,330,507 A | 7/1994 | Schwartz | 607/14 |
| 5,331,966 A | 7/1994 | Bennett et al. | 128/696 |
| 5,345,362 A * | 9/1994 | Winkler | 361/681 |
| 5,354,316 A | 10/1994 | Keimel | 607/15 |
| 5,545,186 A | 8/1996 | Olson et al. | 607/14 |
| 5,690,686 A | 11/1997 | Min et al. | 607/5 |
| 5,800,465 A | 9/1998 | Thompson et al. | 607/9 |

* cited by examiner

IMPLANTABLE MEDICAL DEVICE PROGRAMMING APPARATUS HAVING AN AUXILIARY COMPONENT STORAGE COMPARTMENT

THE FIELD OF THE INVENTION

The present invention relates to portable computer equipment for use with implantable medical devices (IMDs). More particularly, the invention relates to an IMD programmer with a storage compartment configured to store and protect auxiliary components and their associated cables.

BACKGROUND OF THE INVENTION

Implantable medical device systems known in the art comprises several components, including an implantable medical device such as a pacemaker, pacing and/or sensing leads (leads), and a programmer. The leads connect the implantable medical device to the heart of a patient. The programmer provides multiple functions, including (a) assessing lead performance during a pacemaking or defibrillator implantation, (b) programming the implantable medical device, and (c) receiving feedback information from the implantable medical device for use by a clinician or physician (operator). By measuring the electrical performance of a lead during an implant procedure, the programmer aids the operator to select an electrically appropriate site for the placement of the lead(s).

The programmer or programming apparatus is typically portable and generally includes a housing for containing the computer circuitry and other electronic components such as: a power source (e.g., a battery) or at least a cable for connecting the apparatus to a source of power; at least one means for accepting user input (e.g., an alpha-numeric keyboard, a "mouse", or similar devices) and output means (e.g., a text and/or graphic display, a printer, or similar devices) for communicating information to the operator. Additionally, the programming apparatus normally includes one or more auxiliary components for assisting in programming of the implantable medical device. Examples of auxiliary components include a magnetic programming head used to establish a telemetry link between the implanted device and the programmer; patient ECG RF heads for obtaining a patient's surface ECG; a stylus used to interact with a touch screen associated with the programming apparatus; and similar devices. Each of the one or more auxiliary components interface with the computer circuitry via an associated flexible cable. The flexible cable allows the auxiliary component to be maneuvered by the operator to a location slightly spaced from the housing (e.g. in proximity with the patient), yet remain operatively coupled to the computer circuitry.

A programmer for non-invasively programming an implantable medical device, and in particular a cardiac pacemaker, is described in its various aspects in the following U.S. Patents to Hartlaub et al., each commonly assigned to the assignee of the present invention and each incorporated by reference herein: U.S. Pat. No. 4,250,884 entitled "Apparatus For And Method Of Programming The Minimum Energy Threshold For Pacing Pulses To Be Applied To A Patient's Heart"; U.S. Pat. No. 4,273,132 entitled "Digital Cardiac Pacemaker With Threshold Margin Check"; U.S. Pat. No. 4,273,133 entitled "Programmable Digital Cardiac Pacemaker With Means To Override Effects Of Read Switch Closure"; U.S. Pat. No. 4,233,985 entitled "Multi-Mode Programmable Digital Cardiac Pacemaker"; and U.S. Pat. No. 4,253,466 entitled "Temporary And Permanent Programmable Digital Cardiac Pacemaker".

Aspects of the programming apparatus that is the subject of the foregoing Hartlaub et al. patents (hereinafter "the Hartlaub programming apparatus") are also described in U.S. Pat. No. 4,208,008 to Smith entitled "Pacing Generator Programming Apparatus Including Error Detection Means" and in U.S. Pat. No. 4,236,524 to Powell et al., entitled "Programming Testing Apparatus". The Smith '008 and Powell et al. '524 patents are also incorporated by reference herein.

A telemetry system for communicating information either in analog or digital form, between an implanted device and an external programming apparatus is disclosed in U.S. Pat. No. 4,374,382 to Markowitz entitled "Marker Channel Telemetry System For A Medical Device", and in U.S. Pat. No. 4,556,063 to Thompson et al., entitled "Telemetry System For A Medical Device". The Markowitz '382 and Thompson et al., '063 patents are commonly assigned to the assignee of the present invention and are both hereby incorporated by reference herein.

In some cases, a real-time electro cardiogram (ECG) signal may be transmitted from the implanted device to an external unit, so that the physician can monitor the patient's heart activity and the effects of pacing pulses thereon. A pacemaker system having such capability is described, for example, in U.S. Pat. No. RE. 32,361 to Duggen, entitled "Implantable Telemetry Transmission System for Analog and Digital Data", assigned to the assignee of the present invention and incorporated by reference herein.

An example of a programming apparatus incorporating each of the above-features is described in U.S. Pat. No. 5,345,362 to Winkler, entitled "Portable Computer Apparatus With Articulating Display Panel", assigned to the assignee of the present invention and incorporated by reference herein. The Winkler '362 patent describes a programming apparatus having three auxiliary components (i.e., magnetic programming head, stylus, and patient ECG heads) removably stored within a storage compartment formed by the housing. Each of these auxiliary components are operatively coupled to the computer circuitry by flexible cables (best shown in FIG. 9 of the Winkler '362 patent). When not in use, the auxiliary components are stored in the storage compartment, that in turn is enclosed by a separate cover. The storage compartment is sufficiently sized to receive each of the auxiliary components and associated cables. However, due to a relative stiffness and inherent shape of the cables, it is possible that, prior to closure of the cover, portions of one or more of the cables will extend outwardly from the storage compartment along one of the storage compartment's side walls. That is to say, while the cables are inherently flexible, due to a requisite thickness of the conductor cable and surrounding insulation layer, the cables are somewhat rigid and have a natural tendency to revert or unwind to a pre-imparted shape when forced into a small area, such as the storage compartment. Further, the cable(s) are relatively long. Thus, an operator attempting to force a number of relatively long, stiff cables into the storage compartment may not notice a cable section extending out of the storage compartment. As the cover associated with the storage compartment is subsequently closed, the cable(s) is "pinched" between the cover and the housing, likely damaging the cable. While the cable may not be entirely severed, a defect will be introduced into the center conductor, resulting in a break upon subsequent flexing of the cable. In addition, the defect may cause the center conductor to quickly heat during use, again leading to potential failure.

A related potential problem arises during use of the programming apparatus. As previously described, the auxiliary components are removed from the storage compartment, thereby extending the cable(s) across the storage compartment's side walls. With the cables extended, the operator may accidentally close the cover, "pinching" one or more of the cables.

Further, because the storage compartment normally does not include separate retaining assemblies, even when the auxiliary components and cables are properly placed, component damage may occur with transport of the programming apparatus. The auxiliary components are normally not secured within the storage compartment. As a result, movement of the programming apparatus may jar one or more of the auxiliary components, potentially causing damage.

SUMMARY OF THE INVENTION

The present invention overcomes the disadvantages and limitations of the prior art by providing a programming apparatus for use with an implantable medical device including a storage compartment configured to consistently maintain and protect cables associated with auxiliary components.

The present invention provides solutions to certain problems existing in the prior art such as: (a) an inability to maintain and protect auxiliary component cables within a housing storage compartment; (b) an inability to protect auxiliary component cable(s) from damage when the auxiliary component(s) is removed from the housing storage compartment; (c) an inability to minimize auxiliary component and related cable damage during transport of the programming apparatus; and (d) an inability to properly store auxiliary component cable(s) within the storage compartment on an expedited basis.

The apparatus and system of the present invention provides certain advantages, including: (a) the ability to consistently restrain and store auxiliary component cables of a programming apparatus within a housing storage compartment; (b) the ability to minimize the opportunity for auxiliary component cable damage within the housing storage compartment; (c) the ability to minimize the opportunity for auxiliary component cable damage outside of the housing storage compartment; and (d) the ability to minimize damage to the auxiliary components and associated cables during transport of the programming apparatus.

The invention has certain features, including a programming apparatus for use with an implantable medical device. The programming apparatus includes a main housing containing computer circuitry and defining a storage compartment for selectively receiving auxiliary components that interface with the computer circuitry via separate cables. The invention also includes a feature of a lip extending at least partially along the perimeter of the storage compartment, the lip being configured to selectively maintain the cables associated with the auxiliary components during storage. Another feature of the invention is the location of the lip so as to prevent undesirable contact between the auxiliary component cables and a cover otherwise provided to enclose the storage compartment. Yet another feature of the invention is the pliable material forming the lip for minimizing damage upon accidental contact between the cover and the auxiliary component cable. Yet another feature of the invention is the lip forming a gap located to guide the auxiliary component cable outwardly from the storage compartment such that accidental placement of the cover over the storage compartment will not damage the cable. Yet another feature of the invention is the lip facilitating proper storing of the auxiliary component cables on an expedited basis.

Other objects, advantages and features of the invention will become apparent by referring to the appended drawings, detailed description and claims.

DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
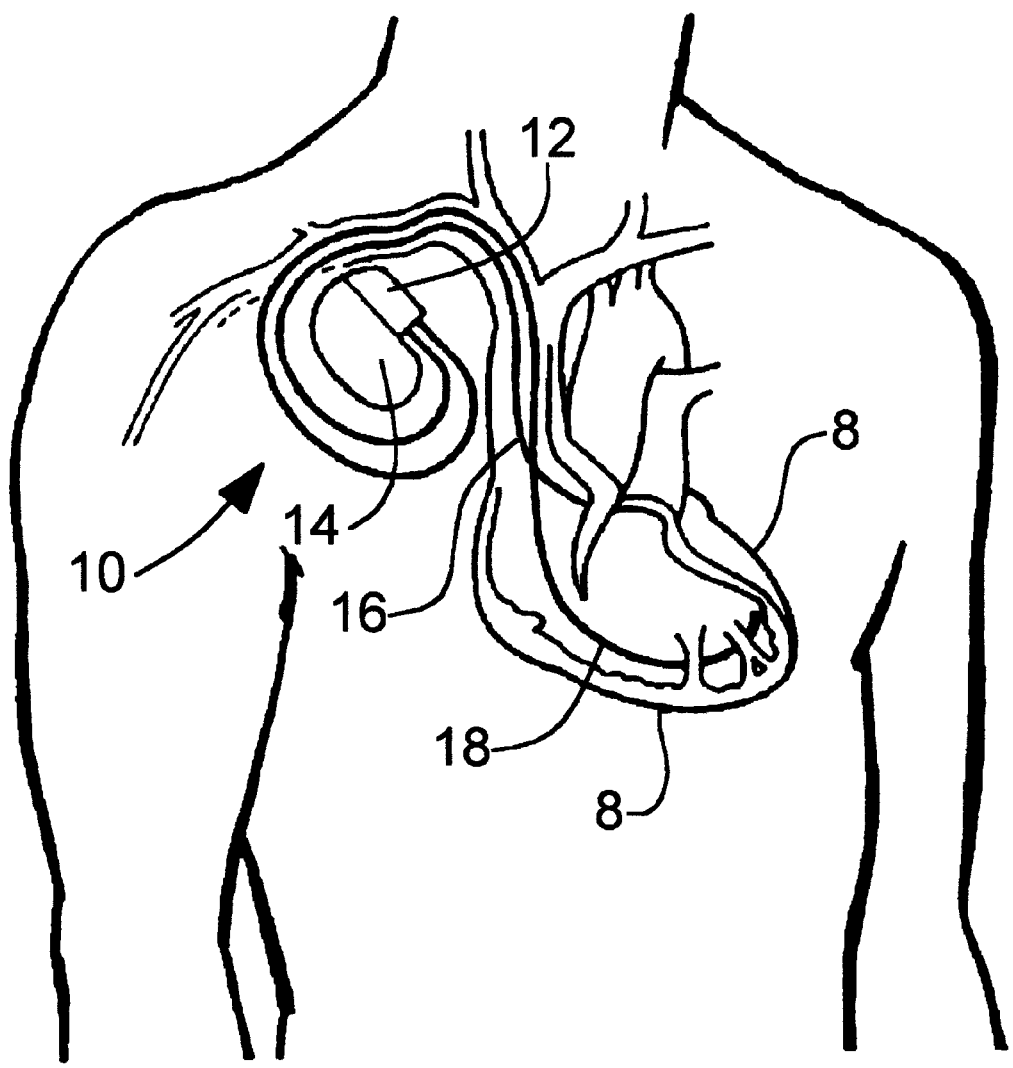
FIG. 1 is a simplified schematic view of one embodiment of an implantable medical device.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158, 078 to Bennett et al., U.S. Pat. No. 5,312,453 to Shelton et al. or U.S. Pat. No. 5,144,949 to Olson, all hereby incorporated by reference herein, each in its respective entirety.

Figure 2:
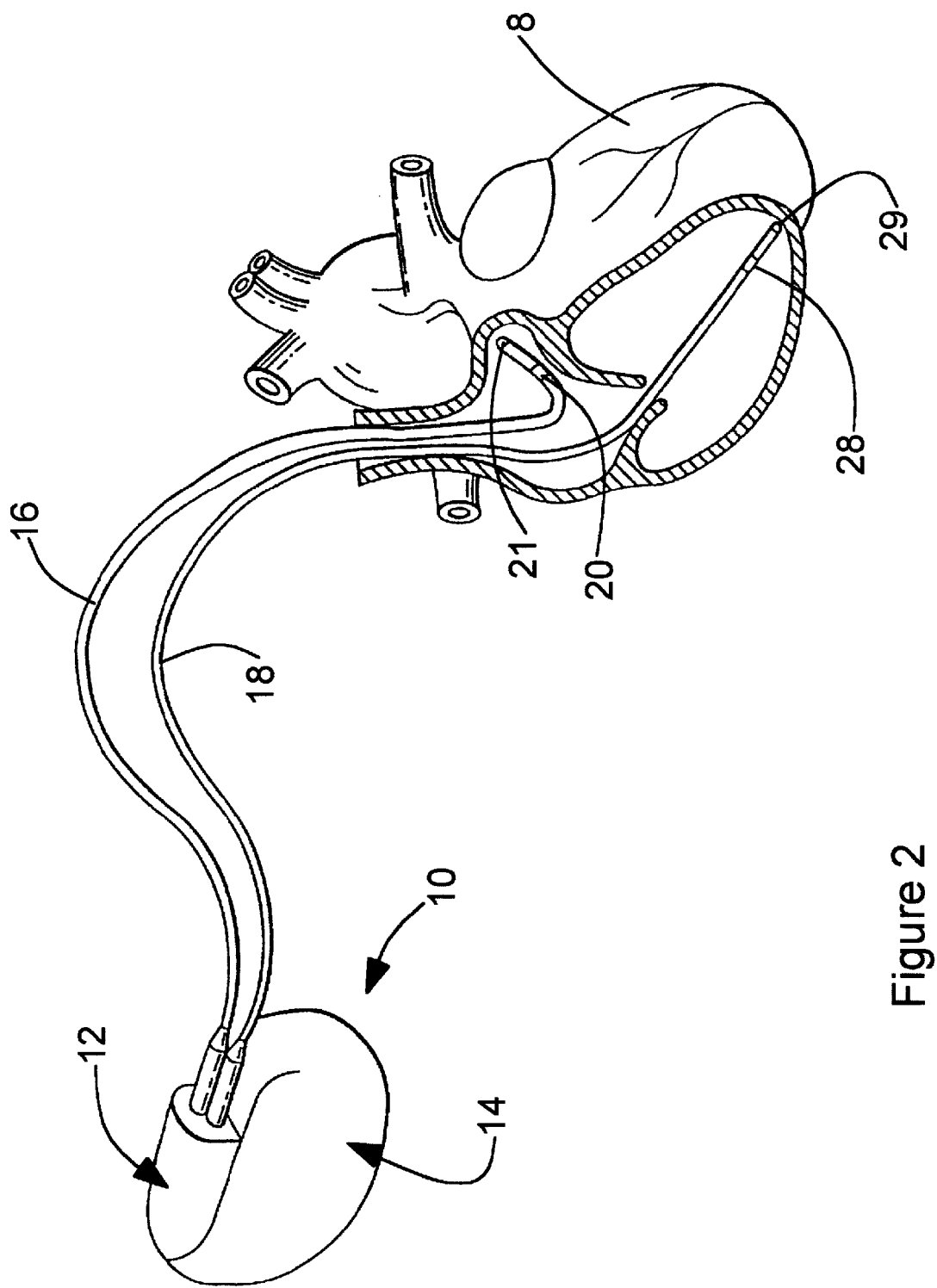
FIG. 2 is a simplified illustration of an implantable medical device with leads positioned within passageways of a heart.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
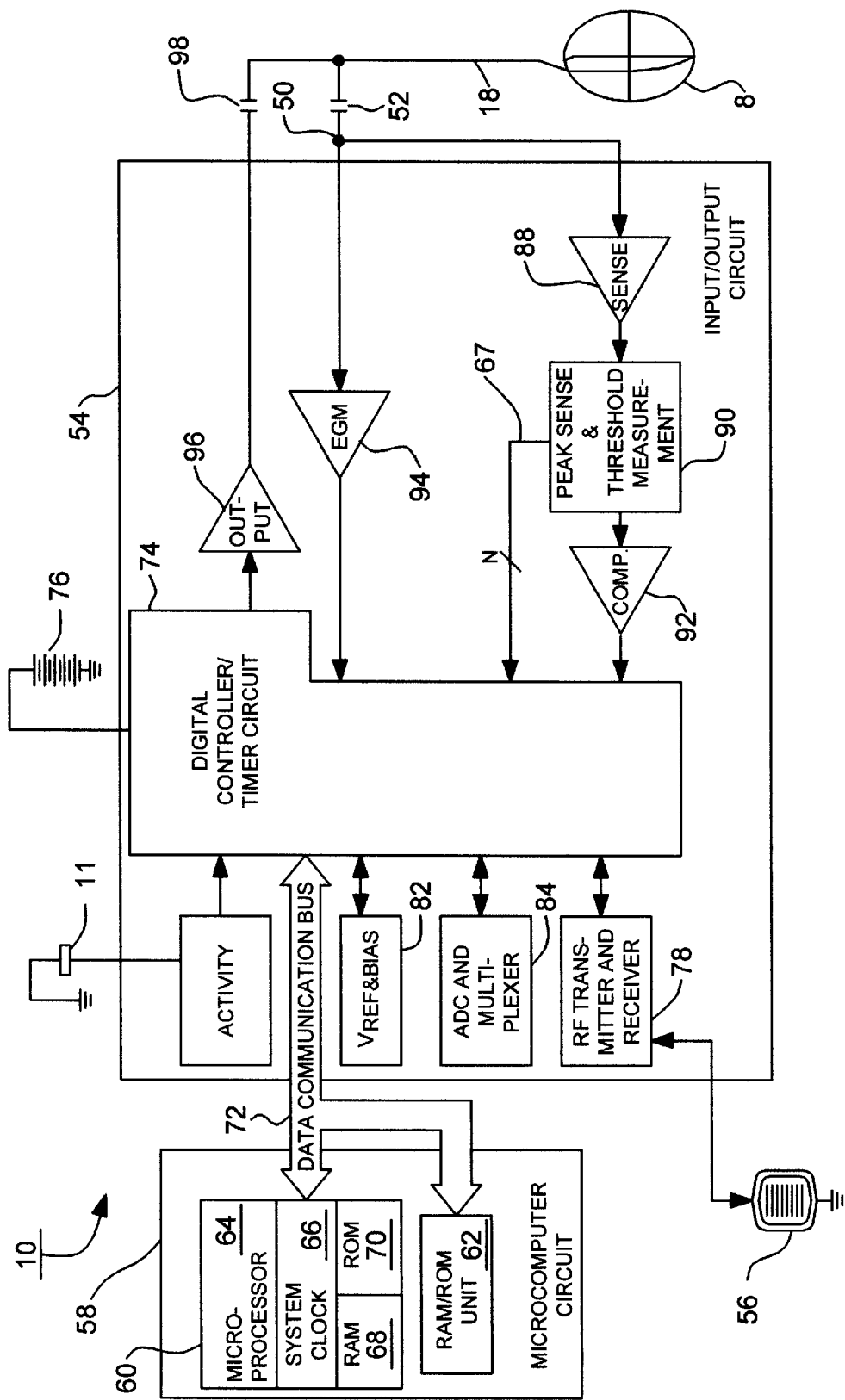
FIG. 3 is a block diagram illustrating the constituent components of an implantable medical device.

FIG. 3 shows a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radiofrequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter- defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 4:
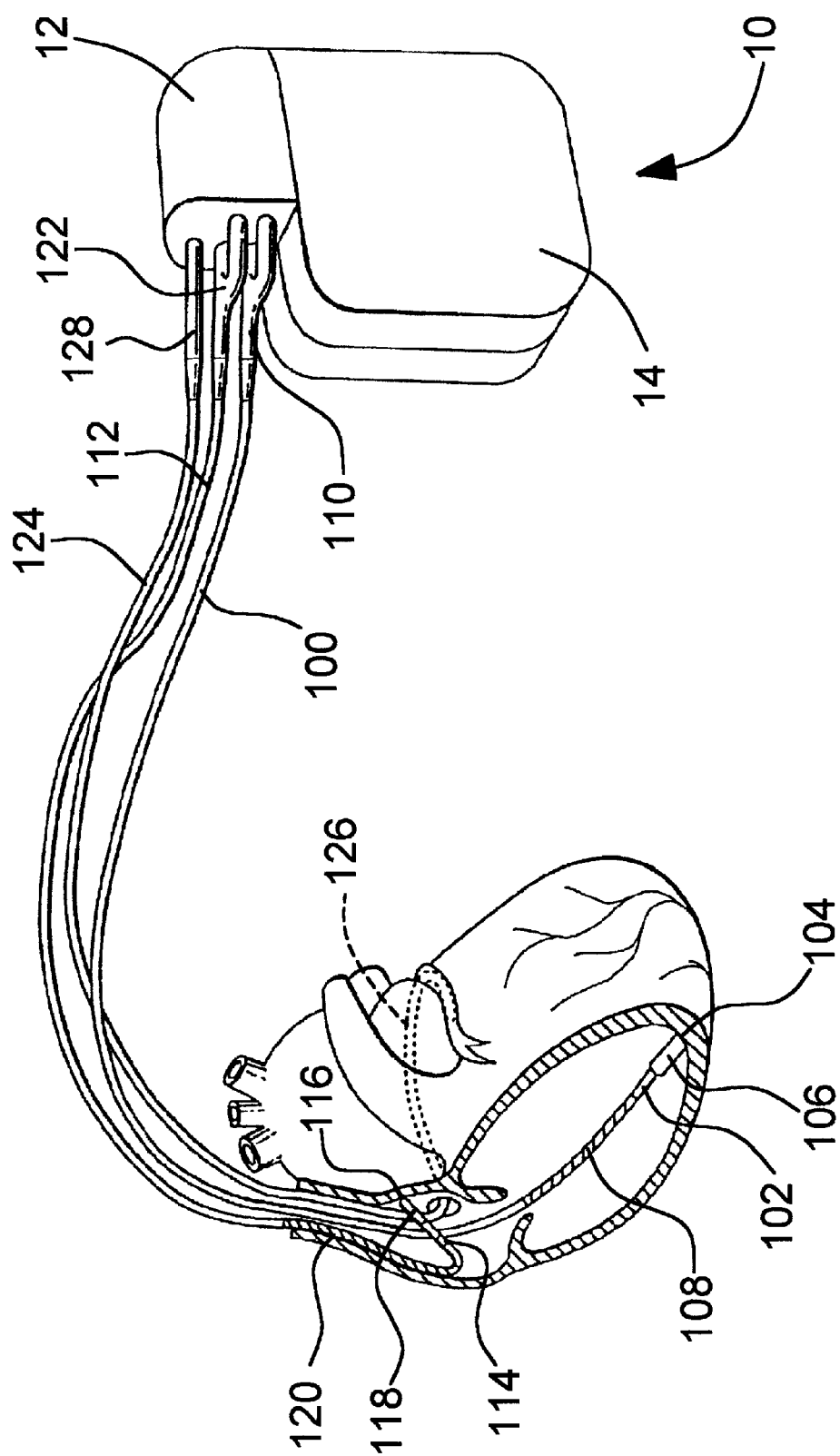
FIG. 4 is a simplified schematic view of an implantable medical device with leads positioned within passageways of a heart.
Figure 5:
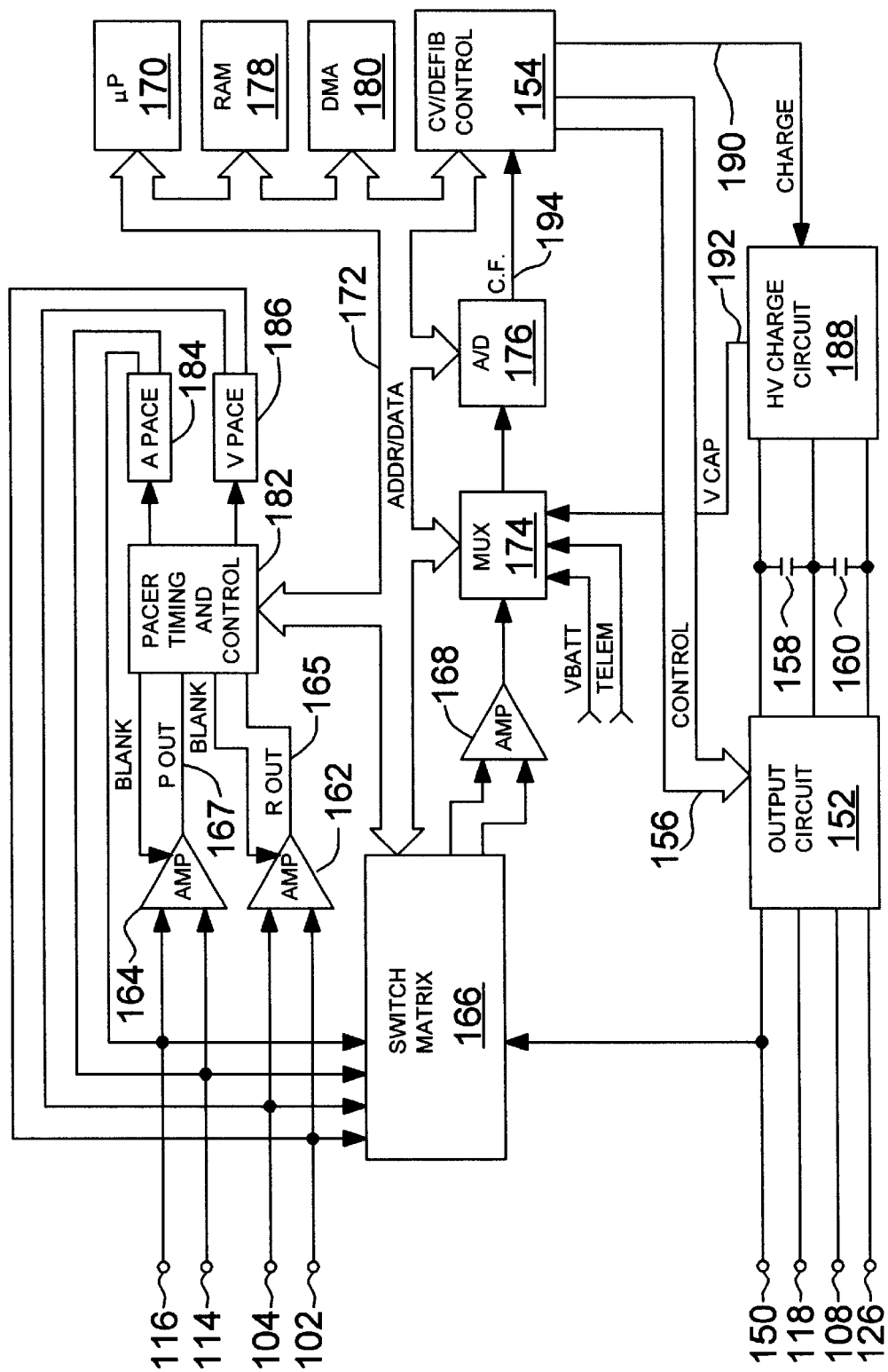
FIG. 5 is a partial block diagram illustrating one embodiment of an implantable medical device used in conjunction with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 100 carrying three concentric coiled conductors separated from one another by tubular insulative sheaths. Located adjacent the distal end of lead 100 are a ring electrode 102, extendable helix electrode 104 mounted retractably within insulative electrode head 106 and elongated coil electrode 108. Each of the electrodes is coupled to one of the coiled conductors within lead body 100. Electrodes 102 and 104 are employed for cardiac pacing and for sensing ventricular depolarizations. At the proximal end of the lead is bifurcated connector 110 which carries three electrical connectors, each coupled to one of the coiled conductors. Defibrillation electrode 108 may be fabricated from platinum, platinum alloy or other materials known to be usable in implantable defibrillation electrodes and may be about 5 cm in length.

The atrial/SVC lead shown in FIG. 4 includes elongated insulative lead body 112 carrying three concentric coiled conductors separated from one another by tubular insulative sheaths corresponding to the structure of the ventricular lead. Located adjacent the J-shaped distal end of the lead are ring electrode 114 and extendable helix electrode 116 mounted retractably within an insulative electrode head 118. Each of the electrodes is coupled to one of the coiled conductors within lead body 112. Electrodes 116 and 114 are employed for atrial pacing and for sensing atrial depolarizations. Elongated coil electrode 120 is provided proximal to electrode 114 and coupled to the third conductor within lead body 112. Electrode 120 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 122 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 124 carrying one coiled conductor coupled to an elongated coiled defibrillation electrode 126. Electrode 128, illustrated in broken outline in FIG. 4, is located within the coronary sinus and great vein of the heart. At the proximal end of the lead is connector plug 128 carrying an electrical connector coupled to the coiled conductor. The coronary sinus/great vein electrode 126 may be about 5 cm in length.

Implantable PCD 10 is shown in FIG. 4 in combination with leads 100, 112, 124, and lead connector assemblies 110, 122 and 128 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 150, 118, 108 and 126 are coupled to high voltage output circuit 152, which includes high voltage switches controlled by CV/defib control logic 154 via control bus 156. Switches disposed within circuit 152 determine which electrodes are employed and which electrodes are coupled to the positive and negative terminals of the capacitor bank (which includes capacitors 158 and 160) during delivery of defibrillation pulses.

Electrodes 102 and 104 are located on or in the ventricle and are coupled to the R-wave amplifier 162, which preferably takes the form of an automatic gain controlled amplifier providing an adjustable sensing threshold as a function of the measured R-wave amplitude. A signal is generated on R-out line 165 whenever the signal sensed between electrodes 102 and 104 exceeds the present sensing threshold.

Electrodes 114 and 116 are located on or in the atrium and are coupled to the P-wave amplifier 164, which preferably also takes the form of an automatic gain controlled amplifier providing an adjustable sensing threshold as a function of the measured P-wave amplitude. A signal is generated on P-out line 167 whenever the signal sensed between electrodes 114 and 116 exceeds the present sensing threshold. The general operation of R-wave and P-wave amplifiers 162 and 164 may correspond to that disclosed in U.S. Pat. No. 5,117,824, by Keimel et al., issued Jun. 2,1992, for "An Apparatus for Monitoring Electrical Physiologic Signals", hereby incorporated by reference herein in its entirety.

Switch matrix 166 is used to select which of the available electrodes are coupled to wide band (0.5–200 Hz) amplifier 168 for use in digital signal analysis. Selection of electrodes is controlled by the microprocessor 170 via data/address bus (ADDR/DATA) 172, which selections may be varied as desired. Signals from the electrodes selected for coupling to bandpass amplifier 168 are provided to multiplexer 174, and thereafter converted to multi-bit digital signals by A/D converter 176, for storage in random access memory 178 under control of direct memory access circuit 180. Microprocessor 170 may employ digital signal analysis techniques to characterize the digitized signals stored in random access memory 178 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 182 preferably includes programmable digital counters which control the basic time intervals associated with DDD, VVI, DVI, VDD, AAI, DDI and other modes of single and dual chamber pacing well known to the art. Circuitry 182 also preferably controls escape intervals associated with anti-tachyarrhythmia pacing in both the atrium and the ventricle, employing any anti-tachyarrhythmia pacing therapies known to the art.

Intervals defined by pacing circuitry 182 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 170, in response to stored data in memory 178 and are communicated to pacing circuitry 182 via address/data bus 172. Pacer circuitry 182 also determines the amplitude of the cardiac pacing pulses under control of microprocessor 170.

During pacing, escape interval counters within pacer timing/control circuitry 182 are reset upon sensing of R-waves and P-waves as indicated by a signals on lines 165 and 167, and in accordance with the selected mode of pacing on time-out trigger generation of pacing pulses by pacer output circuitry 184 and 186, which are coupled to electrodes 114, 116, 102 and 104. Escape interval counters are also reset on generation of pacing pulses and thereby control the basic timing of cardiac pacing functions, including anti-tachyarrhythmia pacing. The durations of the intervals defined by escape interval timers are determined by microprocessor 170 via data/address bus 172. The value of the count present in the escape interval counters when reset by sensed R-waves and P-waves may be used to measure the durations of R-R intervals, P-P intervals, P-R intervals and R-P intervals, which measurements are stored in memory 178 and used to detect the presence of tachyarrhythmias.

Microprocessor 170 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 172. Any necessary mathematical calculations to be performed by microprocessor 170 and any updating of the values or intervals controlled by pacer timing/control circuitry 182 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May–June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 170 into the pacer timing and control circuitry 182, to control the operation of the escape interval counters therein and to define refractory periods during which detection of R-waves and P-waves is ineffective to restart the escape interval counters.

Alternatively, circuitry for controlling the timing and generation of antitachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 170 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 170 activates cardioversion/defibrillation control circuitry 154, which initiates charging of the high voltage capacitors 158 and 160 via charging circuit 188, under the control of high voltage charging control line 190. The voltage on the high voltage capacitors is monitored via VCAP line 192, which is passed through multiplexer 174 and in response to reaching a predetermined value set by microprocessor 170, results in generation of a logic signal on Cap Full (CF) line 194 to terminate charging. Thereafter, timing of the delivery of the defibrillation or cardioversion pulse is controlled by pacer timing/control circuitry 182. Following delivery of the fibrillation or tachycardia therapy microprocessor 170 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Patent No. 4,375,817 to Engle et al., all hereby incorporated by reference herein in their entireties, may also be employed.

Continuing to refer to FIG. 5, delivery of cardioversion or defibrillation pulses is accomplished by output circuit 152 under the control of control circuitry 154 via control bus 156. Output circuit 152 determines whether a monophasic or biphasic pulse is delivered, the polarity of the electrodes and which electrodes are involved in delivery of the pulse. Output circuit 152 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Figure 6:
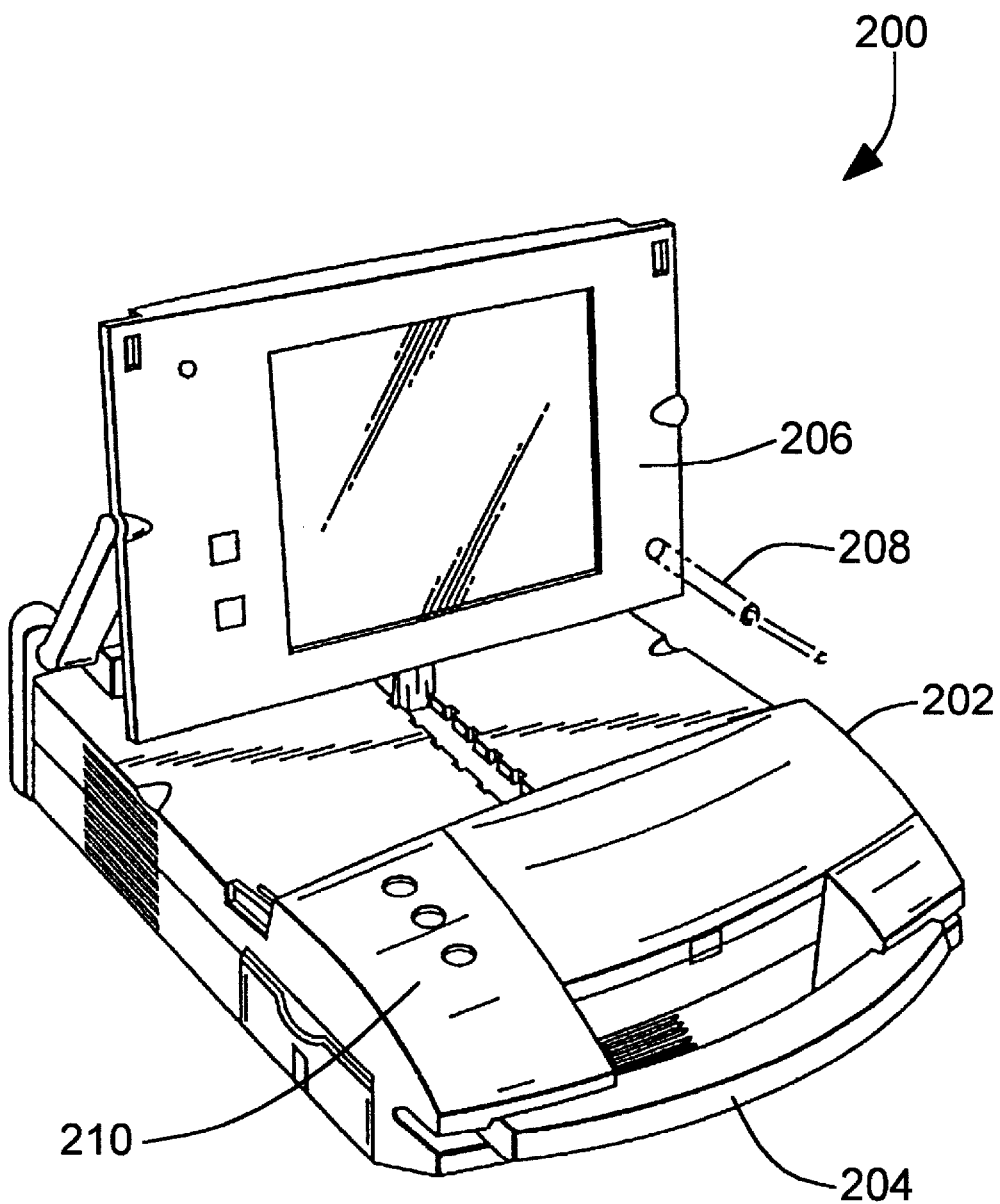
FIG. 6 is a perspective view of a programming apparatus used in conjunction with an implantable medical device.

FIG. 6 is a perspective view of programmner unit or programming apparatus 200 which includes the present invention. Programming apparatus 200 has various features, including outer housing 202, carrying handle 204, articulate display screen 206, stylus 208, and analyzer 210.

Display unit 206 is disposed on the upper surface of housing 202. Display screen 206 folds down in a closed position when programming apparatus 200 is not in use, thereby reducing the size of programming apparatus 200 and protecting the display surface of display screen 206 during transportation and storage. In the perspective view of FIG. 6, programming apparatus 200 is shown with articulate display screen 206 having been lifted up into one of a plurality of possible open positions such that the display area is visible to a user situated in front of programming apparatus 200. Display screen 206 is preferably an LCD or electroluminescent type, characterized by being relatively thin as compared to a cathode ray tube display, or the like. Display screen 206 is operatively coupled to computer circuitry disposed within housing 202 and is adapted to provide a visual display of graphics and/or numerical and alphanumeric data under control of the computer circuitry.

In accordance with one aspect of the present invention, display screen 206 is provided with touch-sensitivity capability, such that a user can interact with the internal computer by touching the display area of display screen 206 with stylus 208. It is believed that those of ordinary skill in the computer art will be familiar with touch-sensitivity display technology, and the details of implementation of such display will not be described further herein. Display screen 206 is the primary input medium for programmer 200, and therefore preferably has sufficient resolution to support operations including selection, gestures, annotation, and character recognition.

Analyzer 210, which in prior art devices is a separate unit capable of connection to programming apparatus 200 only via connecting cables, provides a medium for an operator to run a series of diagnostic tests during an implantation procedure of an IMD, such as IMD 10 previously discussed. For example, a continuous-time waveform or a single complex waveform can be analyzed by analyzer 210 and displayed on display screen 206 from a variety of implanted leads, such as a lead positioned in an atrium or ventricle of heart 8 (shown in FIGS. 1, 2 and 4).

Figure 7:
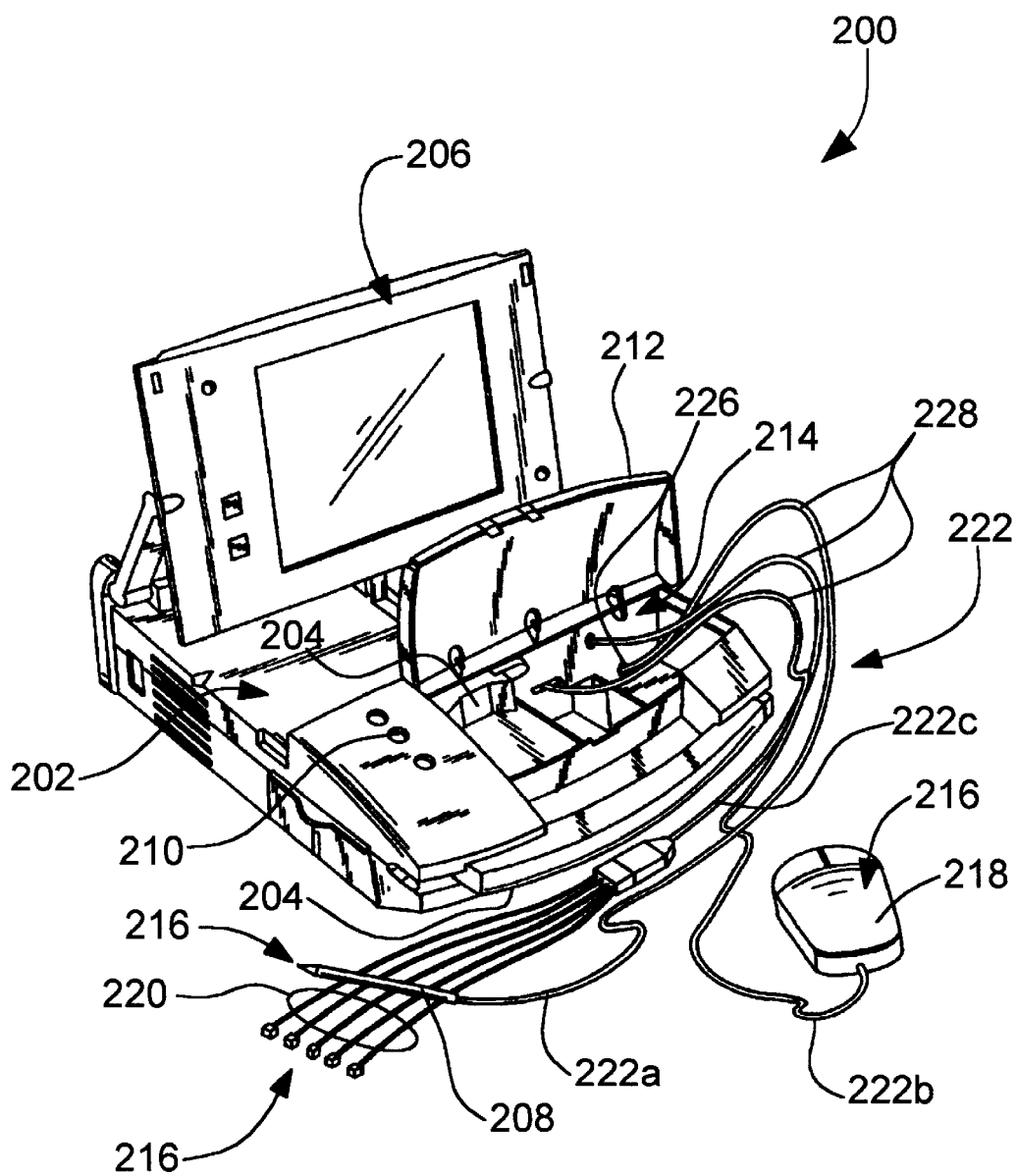
FIG. 7 is a perspective view of the programming apparatus of FIG. 6, showing auxiliary components and a storage compartment.

As best shown in FIG. 7, programming apparatus 200 further includes cover 212, storage compartment 214, and auxiliary components 216. Cover 212 is configured to selectively enclose storage compartment 214 formed by housing 202. In one preferred embodiment, auxiliary components 216 includes stylus 208, magnetic programming head 218 and plurality of patient ECG leads 220. Each of auxiliary components 216 is operatively coupled to, and interfaces with, computer circuitry (not shown) by wiring cables referred to generally by 222, respectively. Auxiliary components 216 and associated cables 222 are selectively storable within storage compartment 214. To this end, programming apparatus 200 further includes lip 224 formed within storage compartment 214 for selectively maintaining auxiliary components 216 and related cables 222, as described in greater detail below.

Auxiliary components 216 are in no way limited to stylus 208, magnetic programming head 218, and patient ECG leads 220. For example, depending upon the desired application of programming apparatus 200, other auxiliary components can be provided and/or one or more of stylus 208, programming head 218 or patient ECG leads 220 can be eliminated. Regardless, auxiliary components 216 are configured to assist in programming IMD 10 previously discussed.

For example, stylus 208 is used to interact with display screen 206. Stylus 208 interfaces with computer circuitry within housing 202 via cable 222a. In this regard, cable 222a is operatively coupled to programming apparatus 200 by means of co-axial connector 226.

Magnetic programming head 218, as would be appreciated by those of ordinary skill in the art, is placed over a patient's body near the implant site of an IMD, such as IMD 10 previously discussed, in order to establish a telemetry link between IMD 10 and programming apparatus 200. Such a programming head is disclosed, for example, in the above-reference Hartlaub programmer patents. Programming head 218 interfaces with computer circuitry (not shown) via cable 222b.

Patient ECG leads 220 are well known in the art and are provided for obtaining a patient's surface ECG. Patient ECG leads 220 convey a patient's surface ECG to internal computer circuitry (not shown) of programming apparatus 200, so that the surface ECG can be displayed on display screen 206 or printed out on an ECG printer. Patient ECG leads 220 interface with computer circuitry via cable 222c.

Cables 222 are of a type commonly known in the art and generally comprise a solid strand center conductor wire surrounded by insulating material. Cables 222 are generally flexible and relatively long, thereby allowing an operator (not shown) to easily maneuver auxiliary components 216 away from housing 202 while remaining operatively coupled to computer circuitry (not shown). However, a composition and thickness of the center conductor wire and insulation imparts a shape memory to cables 222. For example, each of cables 222 are depicted in FIG. 7 as including a bend 228. Bends 228 may be imparted into shape memory of cables 222, for example, during long term storage within storage compartment 214. Flexibility of cables 222 allows an operator to easily "straighten" bend 228 during use of auxiliary components 216. However, following use, each of cables 222 has a natural tendency to reform bends 228. Notably, each of cables 222 may include a number of "pre-formed" bends 228. Further, cables 222 are somewhat rigid, such that it is difficult to quickly and consistently force cables 222 to have other desired bends (as would be required to store cables 222 within storage compartment 214).

Cover 212 is depicted in FIG. 7 as being hingedly secure to housing 202 and sized to enclose storage compartment 214 in a closed position (FIG. 6). Alternatively, cover 212 may assume a wide variety of other forms and need not be hinged to housing 202. For example, cover 212 can be entirely removable from housing 202, and selectively placed over storage compartment 214. Further, cover 212 may incorporate additional components useful in the operation of programming apparatus 200.

Figure 8A:
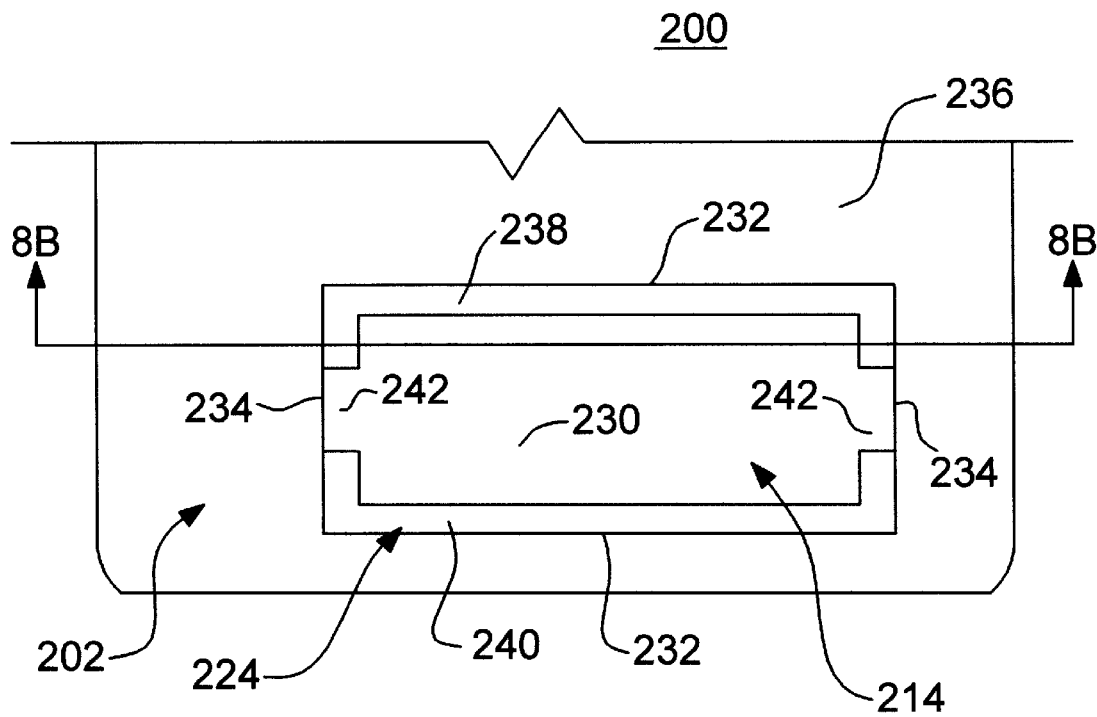
FIG. 8A is a top view of a portion of the programming apparatus of FIG. 7.
Figure 8B:
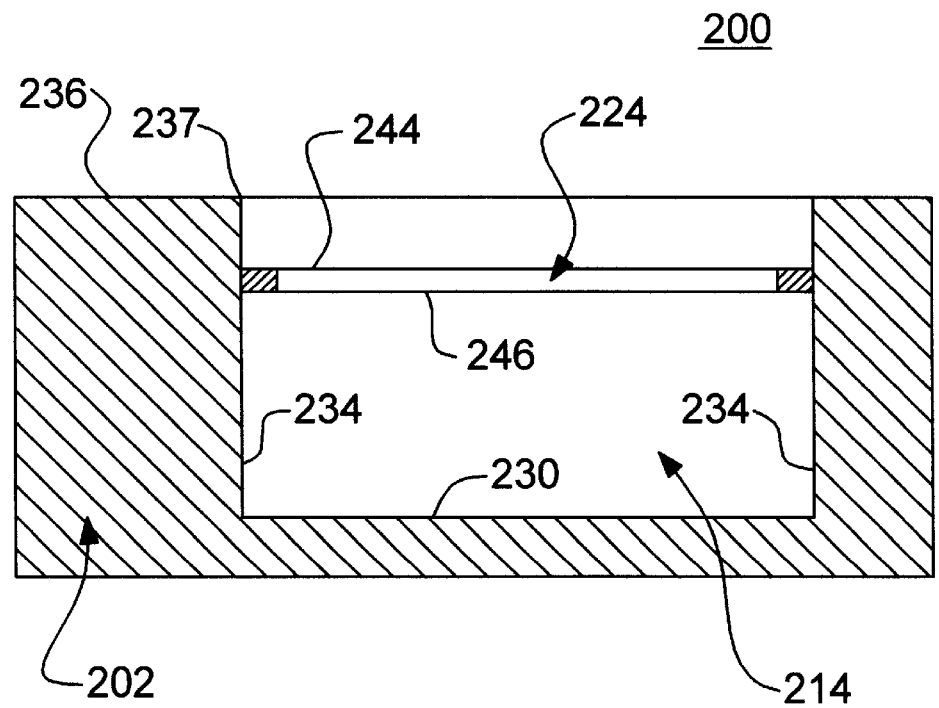
FIG. 8B is a front, cross-sectional view of the programming apparatus of FIG. 7.

Storage compartment 214 and lip 224 are shown in greater detail in FIGS. 8A and 8B. FIG. 8B is a sectional view as seen from line 8B—8B of FIG. 8A. Notably, for ease of illustration, auxiliary components 216 (FIG. 7) and associated cables 222 (FIG. 7) are not shown in FIGS. 8A and 8B. Further, cover 212 has been removed. Storage compartment 214 is defined by bottom wall 230, side walls 232 and end walls 234. Side walls 232 and end walls 234 are preferably integrally formed as a single, continuous wall. As shown best in FIG. 8B, each of side walls 232 and end walls 234 extend upwardly from bottom wall 230, terminating at top surface 236 of housing 202. Upper edge 237 of storage compartment 214 is defined at an intersection of side walls 232/end walls 234 and upper surface 236. Notably, bottom wall 230, side walls 232 and/or end walls 234 need not necessarily be flat as shown, but instead can be contoured to more easily receive and maintain auxiliary components 216.

Lip 224 extends at least partially along a perimeter of storage compartment 214, projecting inwardly from side walls 232 and end walls 234. In one preferred embodiment, and as best shown in FIG. 8A, lip 224 includes first section 238 and second section 240. First section 238 preferably extends along an entirety of one of side walls 232, and along a portion of each of end walls 234. Similarly, second section 240 extends along an entirety of other one of side walls 232, and along a portion of end walls 234. With this configuration, lip 224 preferably forms a gap 242 at each of end walls 234. In other words, gaps 242 are formed between first section 238 and second section 240 of lip 224. Alternatively, only one of gaps 242 need be provided. Even further, gaps 242 can be eliminated entirely such that lip 224 is continuous along a perimeter of storage compartment 214.

As best shown in FIG. 8B, lip 224 defines upper surface 244 and lower surface 246. Lip 224 is preferably disposed within storage compartment 214 such that upper surface 244 is below upper edge 237. In one preferred embodiment, upper surface 244 is spaced from upper edge 237 by a distance in the range of approximately 0.125–0.5 inch; more preferably approximately 0.25 inch. As described below, the spacing between upper surface 244 of lip 224 and upper edge 237 provides an area for receiving cover 212 (FIG. 7). Additionally, lip 224 is positioned and sized such that a sufficient spacing is provided between lower surface 246 and bottom wall 230 for receiving and maintaining auxiliary components 216 (FIG. 7) and associated cables 222 (FIG. 7). In one preferred embodiment, a spacing between lower surface 246 and bottom wall 230 is in the range of approximately 1–3 inches, more preferably approximately 2 inches.

In one preferred embodiment, lip 224 is made of a relatively pliable, non-magnetic material. For example, lip 224 includes a polymer, more preferably an elastomer. Alternatively, in one preferred embodiment, lip 224 includes natural rubber. Regardless of exact material, use of a polymer, and in particular an elastomer, renders lip 224 slightly pliable or deformable, such that lip 224 does not present a rigid corner or surface to auxiliary components 216 (FIG. 7) and/or associated cables 222 (FIG. 7). Additionally, by incorporating a non-magnetic material, lip 224 will not interfere with signals sent to or from auxiliary components 216 along cables 222. Conversely, however, lip 224 is somewhat stiff such that lip 224, and in particular lower surface 246, serves as a "stop" for retaining portions of cables 222 upon storage thereof, as described in greater detail below. With these preferred characteristics in mind, in one preferred embodiment, lip 224 is a rubber elastomer having a thickness in the range of approximately 0.001–0.2 inch; more preferably approximately 0.090 inch. It should be understood, however, that other materials and/or dimensions are equally acceptable.

Lip 224 can be secured to side walls 232 and end walls 234 of storage compartment 214 by a variety of fastening techniques. For example, lip 224 can be adhered to side walls 232 and end walls 234 with an appropriate adhesive. A mechanical fastener, such as a screw or a bolt, can alternatively be employed. Regardless, lip 224 is preferably positioned along a perimeter of storage compartment 214 such that lower surface 246 is substantially parallel with bottom wall 230.

Figure 9A:
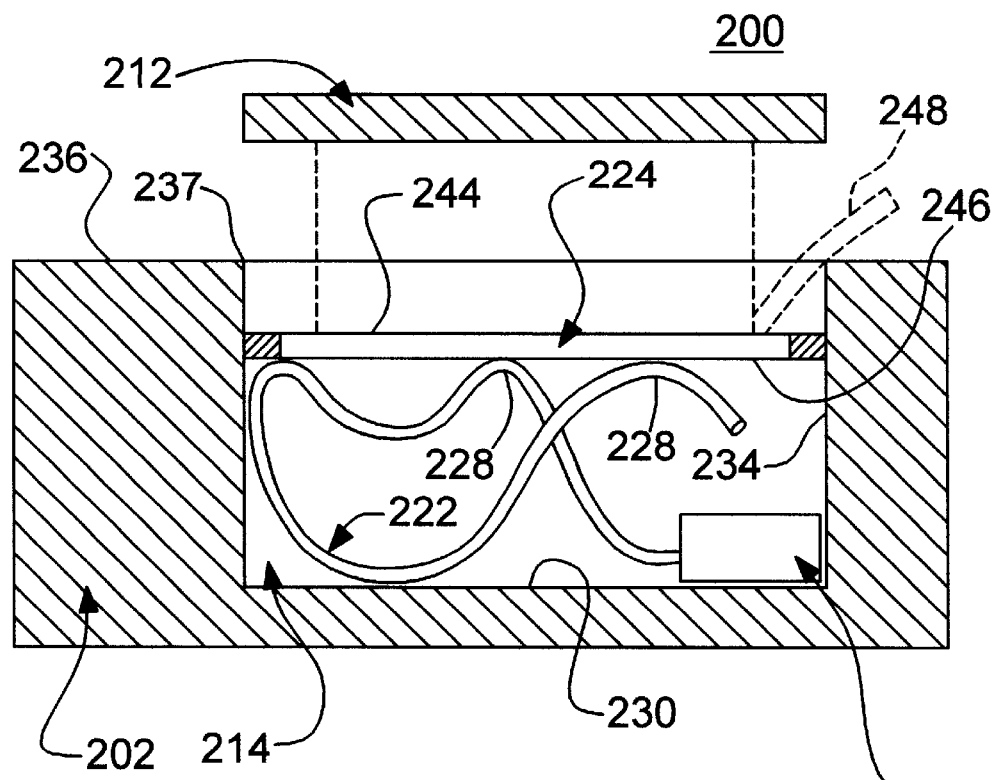
FIG. 9A is a front, cross-sectional view of the programming apparatus of FIG. 7, depicting storage of an auxiliary component and associated cable.

As shown in FIG. 9A, lip 224 is configured to retain cables 222 (one of which is shown) upon placement (or storage) of auxiliary components 216 within storage compartment 214. For ease of illustration, only one of auxiliary components 216 (and therefore one cable 222) is depicted in FIG. 9A. As a point of reference, following use, the operator (not shown) places auxiliary components 216 within storage compartment 214, and then encloses storage compartment 214 with cover 212 for subsequent transport of programming apparatus 200. In the storage position of FIG. 9A, portions of cable 222 abut lower surface 246 of lip 224. As previously noted, cable 222 typically has a shape memory characteristic whereby cable 222 reverts to and forms bends 228. Lip 224 effectively prevents bends 228, and thus cable 222, from projecting outwardly from storage compartment 214, and in particular along upper edge 237 of storage compartment 214. In this regard, lower surface 246 of lip 224 preferably frictionally engages portions of cable 222.

By preventing displacement of cable 222 from storage compartment 214 along upper edge 237, lip 224 will minimize the opportunity for damage to cable 222 upon placement of cover 212, as shown with dotted lines in FIG. 9A. For example, if cable 222 is left unrestrained (as with prior art programming apparatus), a portion 248 will undesirably extend outwardly from storage 214 across top surface 236. As cover 212 is subsequently placed over storage compartment 214, cover 212 will "pinch" portion 248 between cover 212 and top surface 236, resulting in damage to cable 222.

Figure 9B:
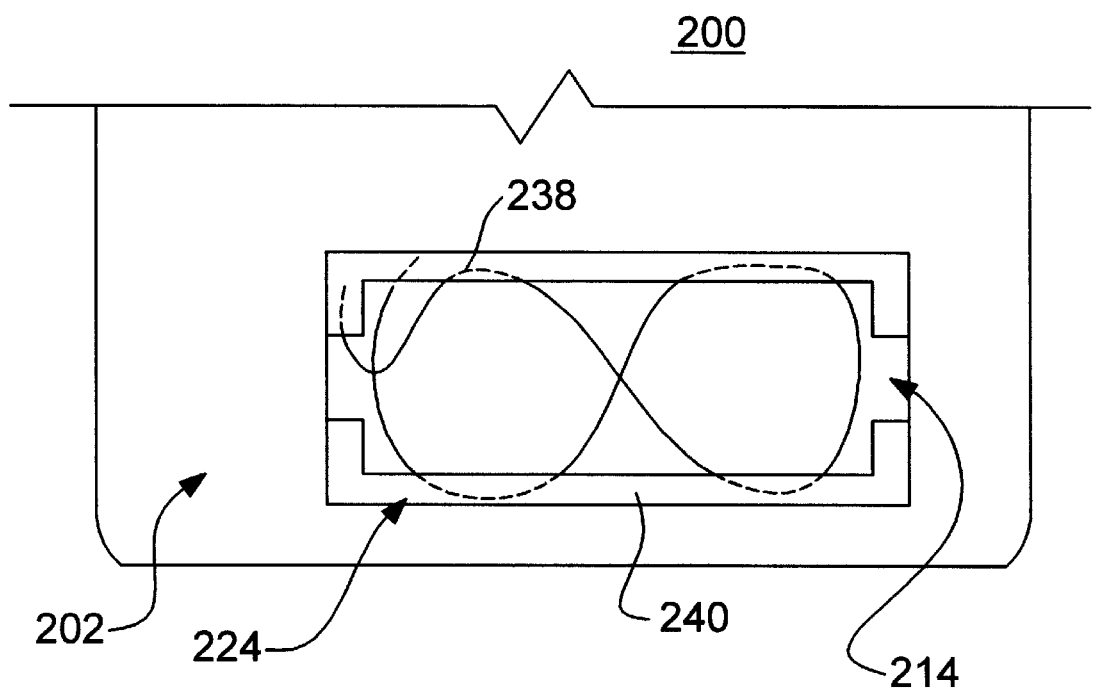
FIG. 9B is a top view of the programming apparatus of FIG. 7, depicting storage of an auxiliary component cable.

Importantly, it is preferably not necessary for lip 224 to prevent projection of cable 222 from storage compartment 214 at a central location thereof. For example, as shown in FIG. 9B, cable 222 is shown as being disposed within storage compartment 214 such that multiple portions 250 extend between first section 238 and second section 240 of lip 224. Due to a shape memory characteristic of cable 222, it is possible that one or more of portions 250 will extend above (or out of the page of FIG. 9B) a height of upper surface 244 (FIG. 9A) of lip 224 and top surface 236 of housing 202. Because portions 250 are effectively spaced from side walls 232 and end walls 234 of storage compartment 214, placement of cover 212 (FIG. 9A) onto storage compartment 214 will not pinch cable 222 against side walls 232 and/or end walls 234. Instead, downward movement of cover 212 toward storage compartment 214 will simply force portions 250 of cable 222 into storage compartment 214. Further, as previously discussed, lip 224 is preferably formed from a pliable material, such that if a portion of cable 222 is unexpectedly located between upper surface 244 of lip 224 and cover 212, lip 224 will deform about cable 222 such that lip 224 does not damage cable 222.

Figure 9C:
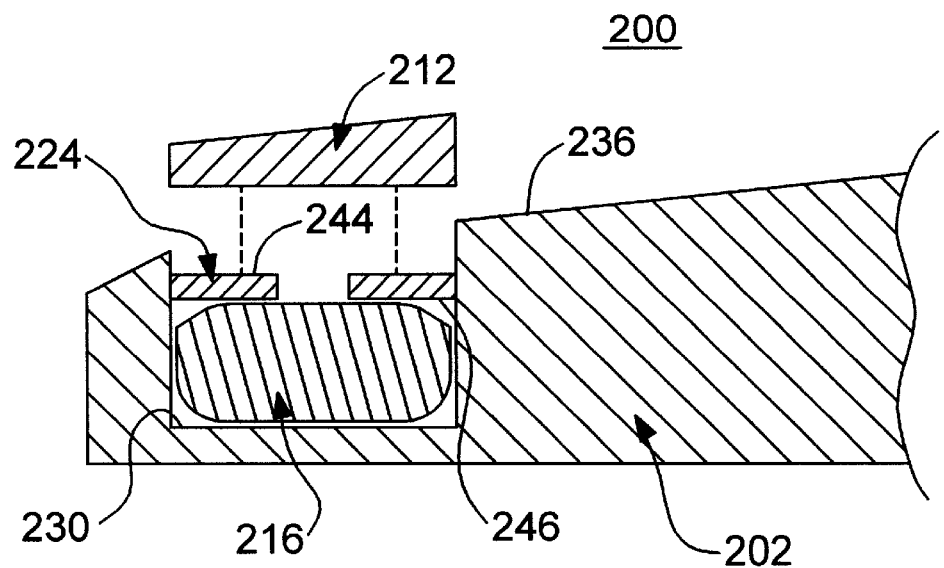
FIG. 9C is a side, cross-sectional view of the programming apparatus of FIG. 7, depicting storage of an auxiliary component.

Depending upon a size of auxiliary component 216 (FIG. 7), lip 224 may also serve to selectively retain auxiliary component 216 within storage compartment 214 as shown in FIG. 9C. FIG. 9C depicts auxiliary component 216 being secured between lip 224 and bottom wall 230 of storage compartment 214. Obviously, the ability of lip 224 to retain one or more of auxiliary components 216 is dependent upon a size and/or height of a particular auxiliary component relative to a spacing between lower surface 246 of lip 224 and bottom wall 230.

An additional feature of lip 224 in one preferred embodiment is providing a surface for receiving cover 212. More particularly, upper surface 244 of lip 224 is preferably configured to receive and maintain cover 212 as shown in FIGS. 9A and 9C. To this end, location of lip 224 preferably corresponds with a thickness of cover 212 such that upon final assembly of cover 212 onto upper surface 244 of lip 224, cover 212 is substantially contiguous with top surface 246 of housing 202.

Figure 10:
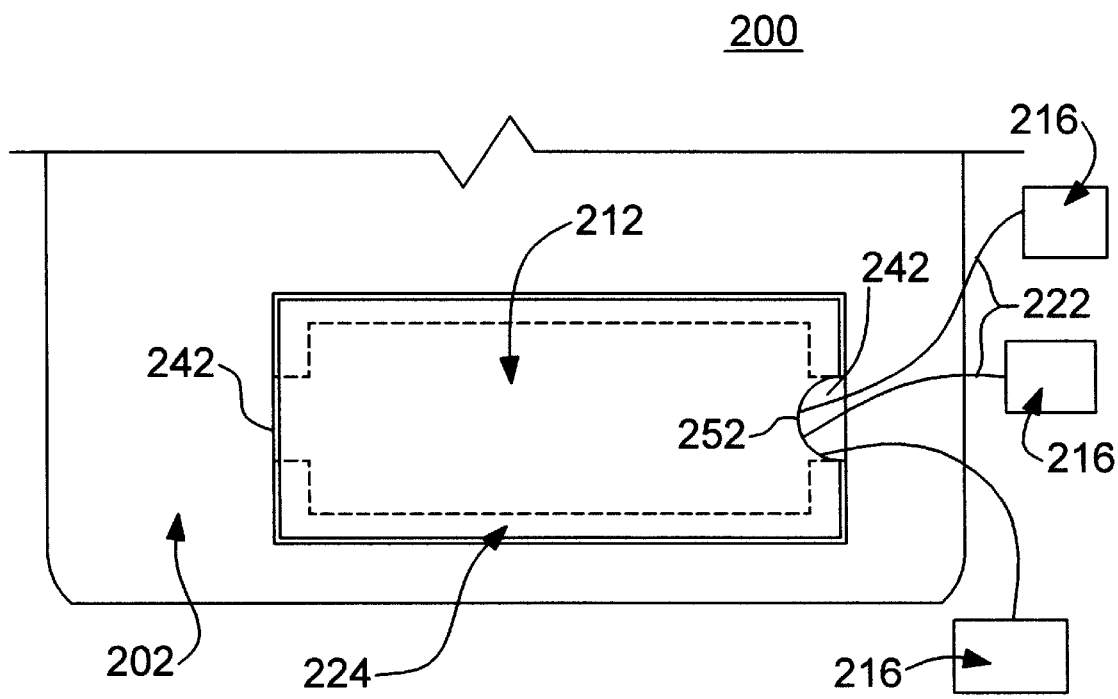
FIG. 10 is a top view of the programming apparatus of FIG. 7 depicting auxiliary components extending from a storage compartment.

It is recognized that during use, it is possible that an operator (not shown) may accidentally attempt to place cover 212 over storage compartment 214 while auxiliary components 216 and associated cables 222 are in use or otherwise extended outwardly from storage compartment 214. As shown best in FIG. 10, gaps 242 formed between first section 238 and second section 240 of lip 224 preferably guide cables 222 from storage compartment 214 at a location whereby cover 212 will impart little or no damage to cables 222. Even further, in one preferred embodiment, cover 212 preferably includes recess 252 forming an opening between cover 212 and side wall 234. Recess 252 preferably corresponds in size and location with at least one of gaps 242. With this configuration, cables 222 freely extend from storage compartment 214 through the opening formed by a combination of gap 242 and recess 252. In other words, unforeseen placement of cover 212 over storage compartment 214 will not damage cables 222 where cables 222 are guided through gap 242.

During use, and with reference to FIG. 7, each of auxiliary components 216 and associated cables 222, are extended from storage compartment 214 and used to assist in programming IMD 10 (FIG. 1). Upon completion, the operator (not shown) replaces each of auxiliary components 216 and associated cables 222 within storage compartment 214. In this regard, because lip 224 projects across only a small portion of storage compartment 214, a large area is provided for convenient placement of auxiliary components 216 and associated cables 222 within storage compartment 214. As part of the storage process, cables 222 are positioned or otherwise packed within storage compartment 214 between lower surface 246 of lip 224 and bottom wall 230. This packing procedure can be done on an expedited basis in that the operator is not required to manually clip or otherwise attach portions of cables 222 to mechanical retaining devices such as a loop-type clip. Instead, cables 222 can be quickly wrapped and then placed within the storage compartment 214, with lip 224 serving as a guide for proper placement. Cover 212 is then placed over storage compartment 214. Because lip 224 retains cables 222 below lower surface 246 thereof, placement of cover 212 onto storage compartment 214 will not pinch or otherwise damage cables 222. Following placement of cover 212, programming apparatus 200 can be moved to other locations without concern for auxiliary component 216 and associated cable 222 damage as auxiliary components 216 and associated cables 222 are retained within storage compartment 214 by lip 224.

The present invention provides a marked improvement over previous programming apparatus designs incorporating a storage compartment to contain auxiliary components. Incorporation of a properly configured lip consistently prevents accidental extension of the cables from the storage compartment that might otherwise result in damage upon closure of the cover, while still allowing expedited component/cable storage. Further, in one preferred embodiment, the lip is configured to provide a guide area or gap to direct the cables in such a way that cable damage will not occur where the cover is accidentally closed.

Although specific embodiments of the invention have been set forth herein in some detail, it is understood that this has been done for the purposes of illustration only and is not to be taken as a limitation on the scope of the invention as defined in the appended claims. It is to be understood that various alterations, substitutions, and modifications may be made to the embodiment described herein without departing from the spirit and scope of the appended claims.

What is claimed is:

1. A portable programming apparatus for use with an implantable medical device, the programming apparatus comprising:
   a housing containing computer circuitry and defining a storage compartment;
   at least one auxiliary component and associated cable configured to assist with programming of an implantable medical device, the at least one auxiliary component interfacing with the computer circuitry via said associated cable such that the at least one auxiliary component is selectively moveable relative to the housing; and
   a lip extending along at least a portion of a perimeter of the storage compartment and extending over the storage compartment to prevent upward movement of the cable.

2. The programming apparatus of claim 1, wherein the storage compartment is defined by a side wall extending from a bottom wall, the lip projecting inwardly from the side wall to selectively maintain the cable between the lip and the bottom wall.

3. The programming apparatus of claim 2, wherein the side wall terminates in an upper edge opposite the bottom wall, the lip being positioned between the upper edge and the bottom wall.

4. The programming apparatus of claim 3, wherein a top surface of the lip is spaced from the upper edge by approximately 0.25 inch.

5. The programming apparatus of claim 3, wherein the cable extends from the storage compartment in an operational position and is stored within the storage compartment in a storage position, the lip being configured to prevent the cable from contacting the upper edge in the storage position.

6. The programming apparatus of claim 5, wherein a portion of the cable abuts a lower surface of the lip in the storage position.

7. The programming apparatus of claim 1, wherein the lip is configured to frictionally engage at least a portion of the cable.

8. A portable programming apparatus for use with an implantable medical device, the programming apparatus comprising:
   a housing containing computer circuitry and defining a storage compartment;
   at least one auxiliary component and associated cable configured to assist with programming of an implantable medical device, the at least one auxiliary component interfacing with the computer circuitry via said associated cable such that the at least one auxiliary component is selectively moveable relative to the housing; and
   a lip extending along at least a portion of a perimeter of the storage compartment for selectively maintaining the cable within the storage compartment, wherein the lip forms at least one gap along a length thereof, the gap being configured to guide the cable outwardly from the storage compartment.

9. The programming apparatus of claim 1, wherein the lip is configured to selectively maintain the auxiliary component.

10. The programming apparatus of claim 1, further comprising:
    a cover associated with the housing for selectively enclosing the storage compartment in a closed position;
    wherein the lip is configured to prevent the cover from damaging the at least one auxiliary component and the cable in the closed position.

11. A portable programming apparatus for use with an implantable medical device, the programming apparatus comprising:
    a housing containing computer circuitry and defining a storage compartment;
    at least one auxiliary component and associated cable configured to assist with programming of an implantable medical device, the at least one auxiliary component interfacing with the computer circuitry via said associated cable such that the at least one auxiliary component is selectively moveable relative to the housing;
    a lip extending along at least a portion of a perimeter of the storage compartment for selectively maintaining the cable within the storage compartment; and
    a cover associated with the housing for selectively enclosing the storage compartment in a closed position, wherein the lip is configured to prevent the cover from damaging the at least one auxiliary component and the cable in the closed position, and wherein the lip forms a gap along a length thereof and the cover forms a recess corresponding with the gap, such that in the closed position, the cable freely extends from the storage compartment through an opening formed by the gap and the recess.

12. The programming apparatus of claim 1, wherein the lip is formed from a pliable material.

13. The programming apparatus of claim 12, wherein the pliable material is an elastomer.

14. The programming apparatus of claim 1, further comprising:
    a plurality of auxiliary components for assisting in programming of an implantable medical device, each of the plurality of auxiliary components interfacing with the computer circuitry via separate cables, wherein the lip is configured to selectively maintain the separate cables within the storage compartment.

15. The programming apparatus of claim 1, wherein the auxiliary component is selected from the group consisting of a magnetic programming head, a stylus and patient ECG leads.

16. A portable programming apparatus for use with an implantable medical device, the programming apparatus comprising:
    housing means containing computer circuitry and defining a storage compartment;
    cover means for selectively enclosing the storage compartment in a closed position;
    at least one auxiliary component means and associated cable for assisting with programming of an implantable medical device, the at least one auxiliary component means interfacing with the computer circuitry via said associated cable such that the at least one auxiliary component means is selectively moveable relative to the housing means; and
    retaining means, separate from the cover means, extending over the storage compartment and preventing upward movement of the cable from the storage compartment for selectively maintaining the cable within the storage compartment.

17. The programming apparatus of claim 16, wherein the retaining means comprises a lip extending at least partially along a perimeter of the storage compartment.

18. The programming apparatus of claim 17, wherein the storage compartment is defined by a side wall extending from a bottom wall, the lip projecting inwardly from the side wall to selectively maintain the cable between the lip and the bottom wall.

19. The programming apparatus of claim 18, wherein the side wall terminates in an upper edge opposite the bottom wall, the lip being positioned between the upper edge and the bottom wall.

20. The programming apparatus of claim 19, wherein a top surface of the lip is spaced from the upper edge by approximately 0.25 inch.

21. The programming apparatus of claim 18, wherein the cable extends from the storage compartment in an operational position and is stored within the storage compartment in a storage position, the lip being configured to prevent the cable from contacting the upper edge in the storage position.

22. The programming apparatus of claim 21, wherein a portion of the cable abuts a lower surface of the lip in the storage position.

23. The programming apparatus of claim 17, wherein the lip is configured to frictionally engage at least a portion of the cable.

24. A portable programming apparatus for use with an implantable medical device, the programming apparatus comprising:
  housing means containing computer circuitry and defining a storage compartment;
  at least one auxiliary component means and associated cable for assisting with programming of an implantable medical device, the at least one auxiliary component means interfacing with the computer circuitry via said associated cable such that the at least one auxiliary component means is selectively moveable relative to the housing means; and
  retaining means disposed with the storage compartment for selectively maintaining the cable within the storage compartment, wherein the retaining means comprises a lip extending at least partially along a perimeter of the storage compartment, and wherein the lip forms at least one gap along a length thereof, the gap being configured to guide the cable outwardly from the storage compartment.

25. The programming apparatus of claim 17, wherein the lip is configured to selectively maintain the auxiliary component.

26. The programming apparatus of claim 17, further comprising:
  a cover associated with the housing for selectively enclosing the storage compartment in a closed position; and
  wherein the lip is configured to prevent the cover from damaging the at least one auxiliary component and the cable in the closed position.

27. A portable programming apparatus for use with an implantable medical device, the programming apparatus comprising:
  housing means containing computer circuitry and defining a storage compartment;
  at least one auxiliary component means and associated cable for assisting with programming of an implantable medical device, the at least one auxiliary component means interfacing with the computer circuitry via said associated cable such that the at least one auxiliary component means is selectively moveable relative to the housing means;
  retaining means disposed with the storage compartment for selectively maintaining the cable within the storage compartment; and
  a cover associated with the housing for selectively enclosing the storage compartment in a closed position, wherein the lip is configured to prevent the cover from damaging the at least one auxiliary component and the cable in the closed position, and wherein the lip forms a gap along a length thereof and the cover forms a recess corresponding with the gap, such that in the closed position, the cable freely extends from the storage compartment through an opening formed by the gap and the recess.

28. The programming apparatus of claim 17, wherein the lip is formed from a pliable material.

29. The programming apparatus of claim 28, wherein the pliable material is an elastomer.

30. The programming apparatus of claim 17, further comprising:
  a plurality of auxiliary component means for assisting in programming of an implantable medical device, each of the plurality of auxiliary component means interfacing with computer circuitry via separate cables, wherein the lip is configured to selectively maintain the separate cables within the storage compartment.

31. The programming apparatus of claim 16, wherein the auxiliary component means is selected from the group consisting of a magnetic programming head, a stylus and patient ECG leads.

32. An implantable medical device system comprising:
  a programming apparatus comprising:
    a housing containing computer circuitry and defining a storage compartment;
    at least one auxiliary component and associated cable configured to assist with programming of an implantable medical device, the at least one auxiliary component interfacing with the computer circuitry via said associated cable such that the at least one auxiliary component is selectively moveable relative to the housing;
    a lip extending along at least a portion of a perimeter of the storage compartment;
    wherein the lip extends over the storage compartment to prevent upward movement of the cable from the storage compartment; and
  an implantable medical device configured to be programmed by the programming apparatus.

33. The system of claim 32, wherein the storage compartment is defined by a side wall extending from a bottom wall, the lip projecting inwardly from the side wall to selectively maintain the cable between the lip and the bottom wall.

34. The system of claim 33, wherein the side wall terminates in an upper edge opposite the bottom wall, the lip being positioned between the upper edge and the bottom wall.

35. The system of claim 34, wherein a top surface of the lip is spaced from the upper edge by approximately 0.25 inch.

36. The system of claim 34, wherein the cable extends from the storage compartment in an operational position and is stored within the storage compartment in a storage position, the lip being configured to prevent the cable from contacting the upper edge in the storage position.

37. The system of claim 36, wherein a portion of the cable abuts a lower surface of the lip in the storage position.

38. The system of claim 32, wherein the lip is configured to frictionally engage at least a portion of the cable.

39. An implantable medical device system comprising:
   a programming apparatus comprising:
      a housing containing computer circuitry and defining a storage compartment;
      at least one auxiliary component and associated cable configured to assist with programming of an implantable medical device, the at least one auxiliary component interfacing with the computer circuitry via said associated cable such that the at least one auxiliary component is selectively moveable relative to the housing;
      a lip extending along at least a portion of a perimeter of the storage compartment;
      wherein the lip is configured to selectively maintain the cable within the storage compartment; and
   an implantable medical device configured to be programmed by the programming apparatus, wherein the lip forms at least one gap along a length thereof, the gap being configured to guide the cable outwardly from the storage compartment.

40. The system of claim 32, wherein the lip is configured to selectively maintain the auxiliary component.

41. The system of claim 32, further comprising:
   a cover associated with the housing for selectively enclosing the storage compartment in a closed position; and
   wherein the lip is configured to prevent the cover from damaging the at least one auxiliary component and the cable in the closed position.

42. An implantable medical device system comprising:
   a programming apparatus comprising:
      a housing containing computer circuitry and defining a storage compartment;
      at least one auxiliary component configured to assist with programming of an implantable medical device, the at least one auxiliary component interfacing with the computer circuitry via an associated cable such that the at least one auxiliary component is selectively moveable relative to the housing;
      a lip extending along at least a portion of a perimeter of and over the storage compartment;
      wherein the lip is configured to selectively maintain the cable within the storage compartment;
      an implantable medical device configured to be programmed by the programming apparatus; and
      a cover associated with the housing for selectively enclosing the storage compartment in a closed position, wherein the lip is configured to prevent the cover from damaging the at least one auxiliary component and the cable in the closed position, and wherein the lip forms a gap along a length thereof and the cover forms a recess corresponding with the gap, such that in the closed position, the cable freely extends from the storage compartment through an opening formed by the gap and the recess.

43. The system of claim 32, wherein the lip is formed from a pliable material.

44. The system of claim 41, wherein the pliable material is an elastomer.

45. The system of claim 32, further comprising:
   a plurality of auxiliary components for assisting in programming the implantable medical device, each of the plurality of auxiliary components interfacing with the computer circuitry via separate cables, wherein the lip is configured to selectively maintain the separate cables within the storage compartment.

46. The system of claim 32, wherein the auxiliary component is selected from the group consisting of a magnetic programming head, a stylus and patient ECG leads.

47. An implantable medical device system comprising:
   programming means comprising:
      housing means containing computer circuitry and defining a storage compartment;
      display means operatively coupled to the computer circuitry;
      at least one auxiliary component means configured to assist with programming of an implantable medical device, the at least one auxiliary component means interfacing with the computer circuitry via an associated cable such that the at least one auxiliary component means is selectively moveable relative to the housing means;
      retaining means extending over the storage compartment and preventing upward movement of the cable from the storage compartment for selectively maintaining the cable within the storage compartment; and
   an implantable medical device configured to be programmed by the programming means.

48. The system of claim 47, wherein the retaining means comprises a lip extending at least partially along a perimeter of the storage compartment.

49. The system of claim 48, wherein the storage compartment is defined by a side wall extending from a bottom wall, the lip projecting inwardly from the side wall to selectively maintain the cable between the lip and the bottom wall.

50. The system of claim 49, wherein the side wall terminates in an upper edge opposite the bottom wall, the lip being positioned between the upper edge and the bottom wall.

51. The programming apparatus of claim 50, wherein a top surface of the lip is spaced from the upper edge by approximately 0.25 inch.

52. The system of claim 50, wherein the cable extends from the storage compartment in an operational position and is stored within the storage compartment in a storage position, the lip being configured to prevent the cable from contacting the upper edge in the storage position.

53. The system of claim 52, wherein a portion of the cable abuts a lower surface of the lip in the storage position.

54. The system of claim 48, wherein the lip is configured to frictionally engage at least a portion of the cable.

55. An implantable medical device system comprising:
   programming means comprising:
      housing means containing computer circuitry and defining a storage compartment;
      display means operatively coupled to the computer circuitry;
      at least one auxiliary component means configured to assist with programming of an implantable medical device, the at least one auxiliary component means interfacing with the computer circuitry via an associated cable such that the at least one auxiliary component means is selectively moveable relative to the housing means;
      retaining means disposed with the storage compartment for selectively maintaining the cable within the storage compartment; and an implantable medical device configured to be programmed by the programming means, wherein the retaining means comprises a lip extending at least partially along a perimeter of the storage compartment, and wherein the lip forms at least one gap along a length thereof, the gap being configured to guide the cable outwardly from the storage compartment.

56. The system of claim 48, wherein the lip is configured to selectively maintain the auxiliary component.

57. The programming apparatus of claim 48, further comprising:
   a cover associated with the housing for selectively enclosing the storage compartment in a closed position; and
   wherein the lip is configured to prevent the cover from damaging the at least one auxiliary component means and the cable in the closed position.

58. An implantable medical device system comprising:
   programming means comprising:
      housing means containing computer circuitry and defining a storage compartment;
      display means operatively coupled to the computer circuitry;
      at least one auxiliary component means configured to assist with programming of an implantable medical device, the at least one auxiliary component means interfacing with the computer circuitry via an associated cable such that the at least one auxiliary component means is selectively moveable relative to the housing means;
      retaining means disposed with the storage compartment for selectively maintaining the cable within the storage compartment;
      an implantable medical device configured to be programmed by the programming means; and
      a cover associated with the housing for selectively enclosing the storage compartment in a closed position, wherein the retaining means comprises a lip extending at least partially along a perimeter of the storage compartment, and the lip is configured to prevent the cover from damaging the at least one auxiliary component means and the cable in the closed position, and wherein the lip forms a gap along a length thereof and the cover forms a recess corresponding with the gap, such that in the closed position, the cable freely extends from the storage compartment through an opening formed by the gap and the recess.

59. The system of claim 48, wherein the lip is formed from a pliable material.

60. The system of claim 59, wherein the pliable material is an elastomer.

61. The system of claim 48, wherein the programming means further includes a plurality of auxiliary component means for assisting in programming the implantable medical device, each of the plurality of auxiliary component means interfacing with the computer circuitry via separate cables, wherein the lip is configured to selectively maintain the separate cables within the storage compartment.

62. The system of claim 47, wherein the auxiliary component means is selected from the group consisting of a magnetic programming head, a stylus and patient ECG leads.

63. A method of using a programming apparatus for an implantable medical device, the programming apparatus including a housing containing computer circuitry and defining a storage compartment, a cover for selectively enclosing the storage compartment, a lip extending inwardly along at least a portion of a perimeter of the storage compartment, and at least one auxiliary component configured to assist in programming the implantable medical device and interfacing with the computer circuitry via a flexible cable, the method comprising the steps of:
   removing the auxiliary component from the storage compartment, the auxiliary component remaining operatively coupled to the computer circuitry by the cable;
   programming the implantable medical device with the programming device;
   positioning the auxiliary component within the storage compartment;
   restraining the cable within the storage compartment by the lip; and
   enclosing the storage compartment with the cover, wherein the lip extends partially over the storage compartment, preventing upward movement of the cable from the storage compartment, and protects the cable from being damaged by the cover.

64. The method of claim 63, wherein the lip defines an upper surface and a lower surface, and further wherein restraining the cable within the storage compartment further includes the step of abutting at least a portion of the cable against the lower surface.

65. The method of claim 64, wherein the lower surface frictionally engages the cable.

66. A method of using a programming apparatus for an implantable medical device, the programming apparatus including a housing containing computer circuitry and defining a storage compartment, a cover for selectively enclosing the storage compartment, a lip extending inwardly along at least a portion of a perimeter of the storage compartment, and at least one auxiliary component configured to assist in programming the implantable medical device and interfacing with the computer circuitry via a flexible cable, the method comprising the steps of:
   removing the auxiliary component from the storage compartment, the auxiliary component remaining operatively coupled to the computer circuitry by the cable;
   programming the implantable medical device with the programming device;
   positioning the auxiliary component within the storage compartment;
   restraining the cable within the storage compartment by the lip; and
   enclosing the storage compartment with the cover, wherein the lip protects the cable from being damaged by the cover, the lip defining an upper surface and a lower surface, wherein restraining the cable within the storage compartment further includes the step of abutting at least a portion of the cable against the lower surface, and further wherein enclosing the storage compartment with the cover further includes the step of contacting the upper surface of the lip with the cover.

67. A method of using a programming apparatus for an implantable medical device, the programming apparatus including a housing containing computer circuitry and defining a storage compartment, a cover for selectively enclosing the storage compartment, a lip extending inwardly along at least a portion of a perimeter of the storage compartment, and at least one auxiliary component configured to assist in programming the implantable medical device and interfac ing with the computer circuitry via a flexible cable, the method comprising the steps of:

removing the auxiliary component from the storage compartment, the auxiliary component remaining operatively coupled to the computer circuitry by the cable;

programming the implantable medical device with the programming device;

positioning the auxiliary component within the storage compartment;

restraining the cable within the storage compartment by the lip; and enclosing the storage compartment with the cover, wherein the lip protects the cable from being damaged by the cover, the lip defining an upper surface and a lower surface, wherein restraining the cable within the storage compartment further includes the step of abutting at least a portion of the cable against the lower surface, and further wherein the lip forms a gap and the cover forms a recess corresponding with the gap and further wherein removing the auxiliary component from the storage compartment further includes the steps of:

extending the auxiliary component from the storage compartment such that the cable passes through the gap; and placing the cover over the storage compartment, wherein the cable extends through an opening defined by the gap and the recess.

68. The method of claim 63, wherein the programming apparatus further includes a plurality of auxiliary components each configured to assist with programming of the implantable medical device and interfacing with the computer circuitry via a separate cables, the method further comprising the step of:

restraining the separate cables within the storage compartment by the lip.

* * * * *

UNITED STATES PATENT AND TRADEMARK OFFICE
CERTIFICATE OF CORRECTION

PATENT NO. : 6,411,851 B1
DATED : June 25, 2002
INVENTOR(S) : Thomas J. Winkler

It is certified that error appears in the above-identified patent and that said Letters Patent is hereby corrected as shown below:

Column 17,
Lines 12 and 51, delete "component and associated cable configured", replace with -- component configured --.
Lines 15 and 55, delete "via said", replace with -- via an --.

Column 18,
Line 14, delete "component and associated cable configured", replace with -- component configured --.
Lines 16 and 61, delete "via said", replace with -- via an --.
Line 56, delete "cover", delete "position".
Line 58, delete "means and associated cable for assisting with programming", replace with -- means configured to assist with programming --
Line 65, delete "means, separate from the cover means, extending", replace with -- means extending --, Column 19,
Lines 34 and 65, delete "means and associated cable for assisting with programming", replace with -- means configured to assist with programming --.
Line 37, delete "via said", replace with -- via an --.
Line 50, delete "selectively.maintain", replace with -- selectively maintain --

Column 20,
Lines 1 and 43, delete "via said", replace with -- via an --.
Line 39, delete "component and associated cable configured", replace with -- component configured --.

UNITED STATES PATENT AND TRADEMARK OFFICE
CERTIFICATE OF CORRECTION

PATENT NO. : 6,411,851 B1
DATED : June 25, 2002
INVENTOR(S) : Thomas J. Winkler

It is certified that error appears in the above-identified patent and that said Letters Patent is hereby corrected as shown below:

Column 21,
Line 11, delete "component configured", replace with -- component and associated cable configured --.
Line 14, delete "via said", replace with -- via an --.

Signed and Sealed this

Twenty-fifth Day of January, 2005

JON W. DUDAS
*Director of the United States Patent and Trademark Office*